United States Patent
Witowski et al.

(10) Patent No.: US 10,857,031 B2
(45) Date of Patent: Dec. 8, 2020

(54) DISPERSION CONTROL USING CHIRPED MIRRORS IN FEMTOSECOND LASER SYSTEM FOR OPHTHALMIC APPLICATION

(71) Applicant: AMO DEVELOPMENT, LLC, Santa Ana, CA (US)

(72) Inventors: Zenon J. Witowski, Pleasanton, CA (US); Mohammad Saidur Rahaman, Santa Clara, CA (US)

(73) Assignee: AMO Development, LLC, Santa Ana, CA (US)

( * ) Notice: Subject to any disclaimer, the term of this patent is extended or adjusted under 35 U.S.C. 154(b) by 189 days.

(21) Appl. No.: 15/888,997

(22) Filed: Feb. 5, 2018

(65) Prior Publication Data

US 2018/0221200 A1    Aug. 9, 2018

Related U.S. Application Data

(60) Provisional application No. 62/455,459, filed on Feb. 6, 2017.

(51) Int. Cl.
*A61F 9/008* (2006.01)
*H01S 3/081* (2006.01)
(Continued)

(52) U.S. Cl.
CPC ............ *A61F 9/008* (2013.01); *A61F 9/0084* (2013.01); *G02B 5/0816* (2013.01);
(Continued)

(58) Field of Classification Search
CPC ........ G02B 5/816; G02B 5/08; G02B 5/0825; G02B 5/0891; G02B 26/0816;
(Continued)

(56) References Cited

U.S. PATENT DOCUMENTS 9,188,776 B2    11/2015    Vogler et al.
2014/0328365 A1    11/2014    Grujic et al.
(Continued)

FOREIGN PATENT DOCUMENTS

EP    2942847 A1    11/2015
KR    20130045245 A    5/2013
KR    20150090799 A    8/2015

OTHER PUBLICATIONS

Dombi, P., et al., "Pulse Compression with Time-Domain Optimized Chirped Mirrors," Optics Express, Dec. 26, 2005, 13 (26), pp. 10888-10894.

(Continued)

*Primary Examiner* — Robert E. Tallman
(74) *Attorney, Agent, or Firm* — Johnson & Johnson Surgical Vision, Inc.

(57) ABSTRACT

A femtosecond laser system for ophthalmic applications, which employs a number of chirped mirrors in the laser beam delivery system between the laser head and the objective lens. The chirped mirrors perform the dual function of both turning the laser beam in desired directions and compensating for beam broadening due to group delay dispersion (GDD) of the optical elements of the system. Each chirped mirror reflects the laser beam only once. Four chirped mirrors are used, each providing up to −5000 $fs^2$ of negative GDD per bounce, to provide a total of −18,000 $fs^2$ negative GDD to compensate for the positive GDD of +18,000 $fs^2$ introduced by other optical elements in the laser beam delivery system. This eliminates the need for a pulse compressor that would employ a grating pair, prism pair or grism pair, and therefore significantly reduces the size of the system and the alignment requirements.

20 Claims, 1 Drawing Sheet

(51) Int. Cl.
*H01S 3/08* (2006.01)
*G02B 26/08* (2006.01)
*H01S 3/00* (2006.01)
*G02B 5/08* (2006.01)
*G02B 26/10* (2006.01)

(52) U.S. Cl.
CPC ........ *G02B 26/0816* (2013.01); *H01S 3/0057* (2013.01); *H01S 3/08009* (2013.01); *H01S 3/0812* (2013.01); *H01S 3/0816* (2013.01); *A61F 2009/00872* (2013.01); *G02B 26/101* (2013.01)

(58) Field of Classification Search
CPC .. H01S 3/08009; H01S 3/0812; H01S 3/0816; A61F 9/008
See application file for complete search history.

(56) References Cited

U.S. PATENT DOCUMENTS

| | | | |
|---|---|---|---|
| 2015/0062680 A1* | 3/2015 | Vogler | G02B 26/0833 359/206.1 |
| 2015/0214688 A1* | 7/2015 | Song | H01S 3/0057 372/25 |
| 2015/0325972 A1 | 11/2015 | Delaigue et al. | |

OTHER PUBLICATIONS

International Search Report and Written Opinion for Application No. PCT/US2018/016922, dated Jun. 6, 2018, 13 pages.

\* cited by examiner

DISPERSION CONTROL USING CHIRPED MIRRORS IN FEMTOSECOND LASER SYSTEM FOR OPHTHALMIC APPLICATION

CROSS-REFERENCES TO RELATED APPLICATIONS

This application claims the benefit under 35 U.S.C. § 119(e) of U.S. Provisional Patent Application No. 62/455,459, filed Feb. 6, 2017, which is incorporated herein by reference in its entirety.

BACKGROUND OF THE INVENTION

Field of the Invention

This invention relates to a laser device and system for ophthalmic applications, and in particular, it relates to a femtosecond laser system employing chirped mirrors which serve to both control laser pulse dispersion and turn the laser beam in desired directions between the laser head and the objective lens.

Description of Related Art

Pulse lasers emitting ultrashort pulses, e.g. in the range of a few femtoseconds to a few hundred femtoseconds, referred to as femtosecond lasers, have been widely used in ophthalmic applications such as LASIK (laser-assisted in situ keratomileusis) procedures. In a femtosecond laser system for ophthalmic applications, it is desirable to keep the pulse width of the laser pulses arriving at the cornea as short as the pulse width when the pulses are emitted from the laser head, so as to maintain high peak intensity and thus enable tissue cutting at relatively low pulse energy. However, when laser pulses propagate through the laser beam delivery system, which may include beam splitters, beam position scanner, objective lenses, etc., the pulse width increases. This is due to the dispersion phenomenon of the optical media such as glass, where each wavelength travels at a different velocity because the indices of refraction of the glass vary as a function of wavelength. This pulse width broadening occurrence is known as group delay dispersion (GDD).

In conventional femtosecond laser systems, a unit within the system (within the laser head module) referred to as pulse compressor is used to provide a negative group delay dispersion to compensate for the positive group delay dispersion experienced in the beam delivery system. This ensures that the pulse arriving at the cornea is as short as possible. However, the conventional pulse compressor is a large unit inside the laser system and composed of many optical and mechanical components. It also tends to be inaccurate if it needs to compensate for large GDD values. For example, a conventional mechanical pulse compressor uses either a diffraction grating pair or a prism pair or a grism pair to provide negative GDD, and also includes a mechanical actuator, lenses and turning mirrors. It is bulky and can increase the overall size of a laser head by 30-40%. To provide certain variability of the GDD, one of the diffraction gratings or prisms is moved using the actuator. To vary the GDD over a larger range, the movement needs to be larger; while conducting the movement over a large range, the alignment parameters of various optical components must be precisely maintained. This increases the complexity of the alignment. Moreover, sometimes it is not possible to achieve the desired amount of negative GDD using a conventional mechanical pulse compressor.

Chirped mirrors are dielectric mirrors formed of multiple stacked dielectric layers. The thickness and refractive indices of the layers vary with the depth. Light at different wavelengths is reflected at different depth of the layer structure and hence experiences different group delay. Thus, a chirped mirror can produce a negative GDD to a laser pulse. FIG. 2 schematically illustrates the principle of a chirped mirror. To introduce negative GDD, longer wavelengths are reflected at deeper depth of the layers (in FIG. 2, $\lambda_1 < \lambda_2 < \lambda_3$).

Chirped mirrors have been used in laser systems for various purposes. For example, Korean Patent No. KR2015090799A describes a laser system including a laser which provides a laser pulse, a fiber for transmitting the laser pulses, a pulse stretcher between the laser and the fiber, and a pulse compressor between the fiber and a target. The pulse stretcher disperses the laser pulse, the fiber extends the spectrum of the laser pulse during transmission, and the pulse compressor reduces the pulse width of the laser pulse. In various embodiments, the pulse stretcher and pulse compressors each uses a pair chirped mirrors where the beam bounces between the two mirrors multiple times, or a pair of prisms, or a pair of gratings, or a pair of grisms.

U.S. Pat. Appl. Pub. No. 20140328365 describes a femtosecond laser device in which the two end mirrors of the laser resonator are dispersive (or chirped) mirrors to produce an average negative GDD. The laser system also uses a GDD pre-compensation unit disposed between the laser device and the fiber transmission unit, which uses a pair of dispersive mirrors where the beam bounces between the two mirrors multiple times giving a negative dispersion between $-5000$ and $-15000$ $fs^2$.

U.S. Pat. No. 9,188,776 B2 describes an ultra-short pulse laser system which includes a dispersion compensating device for compensating the GDD of other components in the system. The dispersion compensating device includes a deformable, dispersive (or "chirped") mirror, an actuator device for moving the dispersive mirror, and a bulk compensator. The bulk compensator uses a pair of oppositely disposed dispersive mirrors, where the beam bounces between the two mirrors multiple times; it may also use a single dispersive mirror, a pair of gratings or a pair of prisms.

Korean Patent No. KR2013045245A describes a femtosecond laser with adjustable repetition rate, including a stretcher-compressor that employs a chirped volume Bragg grating which stretches the pulse entering one end of the grating and compresses the pulse entering the opposite end of the grating. This patent also shows a design where a laser pulse amplifier with dispersion control, where one or more of the end mirrors or folding mirrors of the resonance cavity are chirped mirrors.

Chirped mirrors, including those used in the above-mentioned references, typically produce a few hundred $fs^2$ of negative GDD per bounce. P. Dombi et al., Pulse compression with time-domain optimized chirped mirrors, 26 Dec. 2005/Vol. 13, No. 26/OPTICS EXPRESS 10888-10894, describes designs of chirped mirrors compressors capable of providing peak-to-peak GDD-oscillations over 2000 $fs^2$ in six mirror bounces in certain wavelength ranges, for generating sub-5-fs pulses. Very high GDD chirped mirrors, such as chirped mirrors that can provide up to $-5000$ $fs^2$ of GDD per bounce in certain wavelength range are commercially available, for example, from NANEO Precision IBS Coatings GmbH.

SUMMARY

The present invention is directed to an apparatus, system and related method that substantially obviates one or more of the problems due to limitations and disadvantages of the related art.

An object of the present invention is to achieve pulse compression using chirped mirrors to provide necessary negative GDD and to eliminate mechanical movements, diffraction gratings or prisms, lenses and a complex alignment process associated with conventional pulse compressors.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides an optical system for directing a pulsed laser beam from a laser to an objective lens, which includes: a plurality of chirped mirrors disposed along an optical path of the pulsed laser beam; and one or more optical elements disposed along the optical path, the optical elements including one or more of: half wave plate, beam splitter, beam sampler, and XY beam position scanner and Z beam position scanner, wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens.

In another aspect, the present invention provides a pulsed laser system for ophthalmic applications, which includes: a laser generating a pulsed laser beam having a pulse width below a few hundred femtoseconds; an objective lens for directing the pulsed laser beam to a patient's eye; an optical system for directing the pulsed laser beam from the laser to the objective lens along an optical path, including: a plurality of chirped mirrors disposed along an optical path of the pulsed laser beam; and one or more optical elements disposed along the optical path, the optical elements including one or more of: half wave plate, beam splitter, beam sampler, XY beam position scanner and Z beam position scanner, wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens.

In one embodiment, the plurality of chirped mirrors consist of four chirped mirrors which provide a combined negative GDD of approximately −18,000 $fs^2$ in the defined wavelength range.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention eliminate the mechanical pulse compressor from the laser head module, and instead use chirped mirrors to provide a negative GDD to compress the laser pulses when they travel in the beam delivery system between the laser head and the objective lens that focuses the beam onto the eye. In a typical beam delivery system, a number of mirrors are used to turn the beam in order to achieve a compact optical system design and/or a desired direction of the output beam. According to embodiments of the present invention, chirped mirrors are used in the beam delivery system to achieve the dual functions of both turning the laser beam to the appropriate directions and providing the required negative GDD to compensate for the pulse broadening. In other words, some or all of the beam turning mirrors in the conventional beam delivery system are replaced by chirped mirrors; additional chirped mirrors may be used as needed to provide the required amount of negative GDD. Each chirped mirror in the beam delivery system reflects the laser beam only once.

Thus, the femtosecond laser system according to embodiments of the present invention eliminates the conventional pulse compressor—including the diffraction gratings or prisms or grisms, lenses, mirrors, and mechanical actuators—without adding many additional optical components to the beam delivery system. This will significantly reduce the size of the laser head. Because fewer optical elements are used in the laser head, the associated alignment requirements are reduced. Further, mechanical or electrical actuators required by conventional pulse compressors are eliminated, which results in a more robust and reliable system.

Femtosecond laser pulses transmitting through the optical components of a laser beam delivery system typically experience a positive GDD close to approximately +18,000 $fs^2$ in the operating wavelength range. Current state of the art chirped mirrors can be manufactured to provide up to −5,000 $fs^2$ of GDD per bounce for femtosecond laser pulses in the wavelength range of about 400 to 1500 nm. In a laser beam delivery system according to an embodiment of the present invention, four such chirped mirrors are used, which replace four or two conventional turning mirrors. For example, the four chirped mirrors may be one pair with approximately −5,000 $fs^2$ of GDD per bounce for each mirror and one pair with approximately −4,000 $fs^2$ of GDD per bounce for each mirror, or two pairs with approximately −4,500 $fs^2$ of GDD per bounce for each mirror, so that the four chirped mirrors provide a total of negative GDD of approximately −18,000 $fs^2$.

Figure 1:
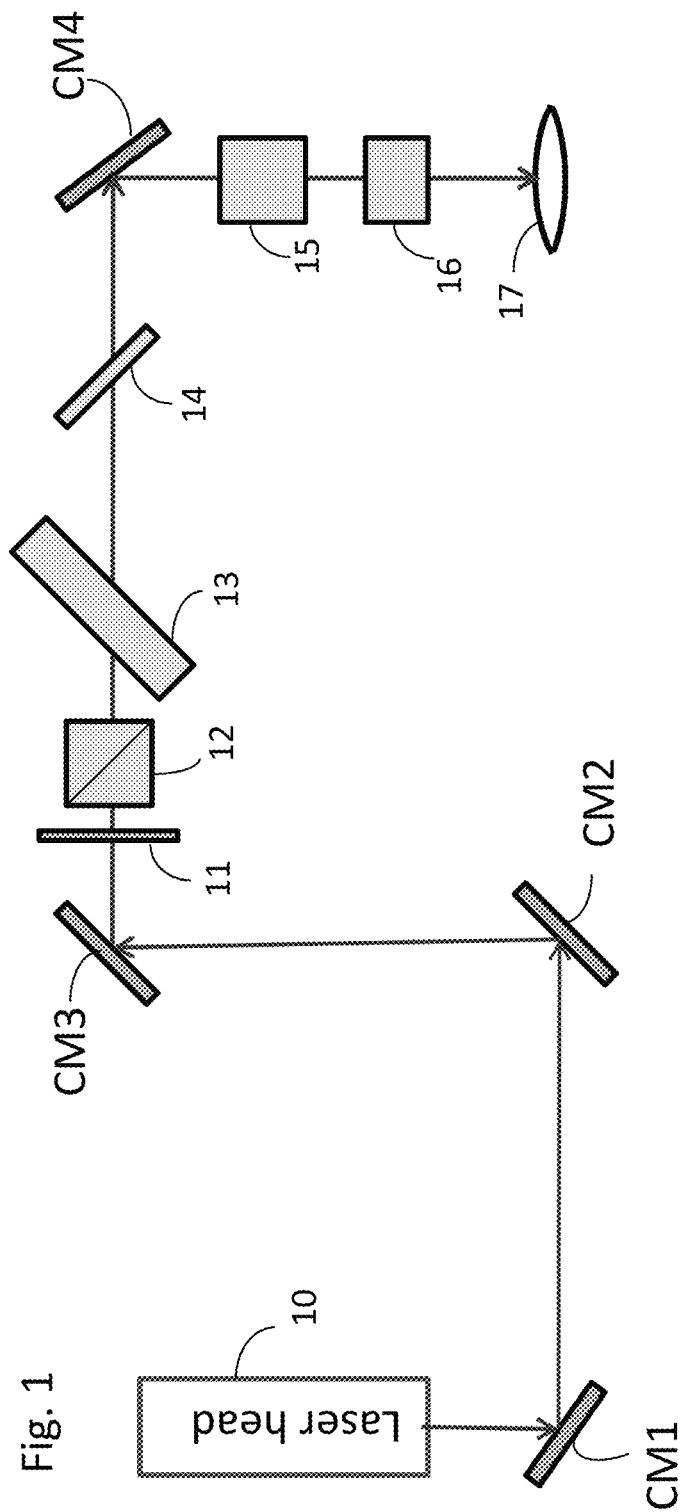
FIG. 1 schematically illustrates a femtosecond laser surgical device including laser head and beam delivery optics including chirped mirrors according to an embodiment of the present invention.
Figure 2:
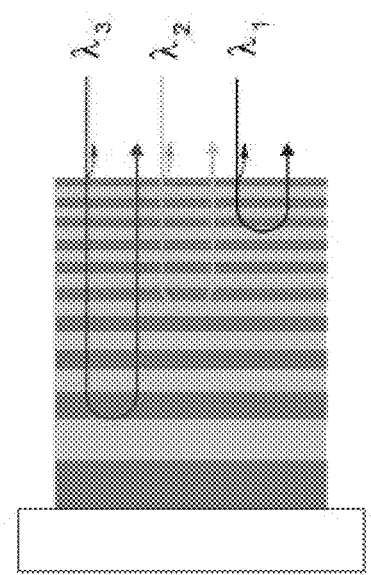
FIG. 2 schematically illustrates a chirped mirror that may be used in embodiments of the present invention.

FIG. 1 schematically illustrates a femtosecond laser system including the laser beam delivery system for ophthalmic applications. The laser 10 is a femtosecond laser capable of generating a pulsed laser beam having a pulse width in the range of a few femtoseconds to a few hundred femtoseconds. The laser 10 does not include a conventional pulse compressor that employs diffraction gratings, prisms or grisms and mechanical actuators.

The beam delivery optical system located between the laser head 10 and the objective lens 17 includes first to fourth chirped mirrors CM1, CM2, CM3 and CM4, disposed in that order in the optical path between the laser head and the objective lens, each reflecting the laser beam only once. A number of other optical elements of the laser beam delivery system are disposed between the first to fourth chirped mirrors CM1 to CM4. In the embodiment illustrated in FIG. 1, a half wave plate 11, a beam splitter 12, a first beam sampler 13 and a second beam sampler 14 are disposed between the third chirped mirror CM3 and the fourth chirped mirror CM4, and beam position scanners such as XY scanner 15 and Z scanner 16 are located between the fourth chirped mirror CM4 and the objective lens 17. In the illustrated embodiment, the first to third chirped mirrors CM1, CM2 and CM3 are disposed upstream of the optical elements 11-14, and the fourth chirped mirror CM4 directs the laser beam from the last one of the optical elements 11-14 to the beam scanners 16 and 17 and then to the objective lens 17 to be delivered to the patient's eye.

In alternative embodiments, some of the optical components 11-14 may be disposed between the laser head 10 and the first chirped mirror CM1, or between the first and second chirped mirrors CM1 and CM2, or between the second and third chirped mirrors CM2 and CM3, or between the fourth chirped mirror CM4 and the objective lens 17. In other alternative embodiments, additional optical elements such as attenuator, beam shaping element and beam expander may be present in the laser delivery optical system and disposed along the optical path from the laser head 10 to the objective lens 17.

Each of the four chirped mirrors CM1 to CM4 provides a GDD of approximately −4,000 to −5,000 fs$^2$ in a single bounce. In one implementation, each of the four chirped mirrors CM1 to CM4 provides approximately −4,500 fs$^2$ of GDD. Other combinations of GDD values may be used, so long as CM1 and CM2 have the same GDD and CM3 and CM4 have the same GDD and the four chirped mirrors CM1 to CM4 add up to approximately −18,000 fs$^2$ of GDD, which is identical in absolute value to the positive GDD of the other optical components 11-17 of the laser beam delivery system.

In the laser beam delivery system according to embodiments of the present invention, each of the chirped mirrors CM1 to CM4 reflects the laser beam only once. The chirped mirrors CM1 to CM4 are fixedly mounted in their respective positions; i.e., they are fixed and are not moved during intended use (i.e. after they have been properly aligned). No actuators are provided to move, either to shift or to rotate, any of the chirped mirrors during intended use. Because the four chirped mirrors CM1 to CM4 provide sufficient negative GDD to compensate for the combined positive GDD of the other optical elements in the optical path, the laser beam delivery system does not include any additional diffraction pulse compressor that would employ grating pairs, prism pairs or grism pairs.

In other embodiments, the combined positive GDD of the other optical elements in the optical path may be a value other than +18,000 fs$^2$, and the negative GDD of the chirped mirrors CM1 to CM4 and the number of chirped mirrors may be selected accordingly so that the combined negative GDD of the chirped mirrors is approximately identical in absolute values to the combined positive GDD of the other optical elements.

When the laser pulse is bounced once by a chirped mirror, the GDD spectrum (i.e. the GDD curve as a function of wavelength) tends to exhibit oscillations over a relatively wide wavelength range. To mitigate the undesirable effect of such oscillations, it is common to use a pair of chirped mirrors that are designed to have their oscillations in the GDD spectra shifted relative to each other, so that after one bounce by each of the two chirped mirrors at identical incident angles, the oscillation behavior of the combined GDD spectrum is significantly reduced. In some conventional optical systems (such as some of those discussed earlier in the Background section), a pair of chirped mirrors are arranged in parallel to each other, and the laser beam is bounced multiple times between the two chirped mirrors.

In preferred embodiments of the present invention, the first and second chirped mirrors CM1 and CM2 are designed as a pair with shifted GDD spectra, and the third and fourth chirped mirrors CM3 and CM4 are designed as a pair with shifted GDD spectra, so that the combined GDD spectrum of each pair has significantly reduced oscillations. The optical path is designed so that the laser beam is incident on the two chirped mirrors in each pair (CM1 and CM2, and CM3 and CM4) at identical incident angles. Note that the two chirped mirrors in each pair do not need to be parallel to each other and they are in fact not parallel to each other in the preferred embodiment.

Chirped mirror pairs can also be designed to correct higher order dispersion effects, providing additional advantage to the beam delivery system of embodiments of the present invention which employ chirped mirror based pulse compression.

It will be apparent to those skilled in the art that various modification and variations can be made in the femtosecond laser system of the present invention and related methods without departing from the spirit or scope of the invention. Thus, it is intended that the present invention cover modifications and variations that come within the scope of the appended claims and their equivalents.

What is claimed is:

1. An optical system for directing a pulsed laser beam from a laser to an objective lens, the optical system comprising:

a plurality of chirped mirrors disposed along an optical path of the pulsed laser beam; and one or more optical elements disposed along the optical path, the optical elements including one or more of: half wave plate, beam splitter, beam sampler, XY beam position scanner and Z beam position scanner, wherein the plurality of chirped mirrors includes a first chirped mirror, a second chirped mirror, a third chirped mirror, and a fourth chirped mirror disposed sequentially in the optical path in an order of from the first to the fourth chirped mirrors, wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens, and wherein the one or more optical elements are disposed between the third and fourth chirped mirrors or between the first and second chirped mirrors.

2. The optical system of claim 1, wherein the first chirped mirror is disposed to receive the pulsed laser beam from the laser.

3. The optical system of claim 1, wherein the fourth chirped mirror is disposed to reflect the pulsed laser beam to the objective lens.

4. A pulsed laser system for ophthalmic applications, comprising:
a laser generating a pulsed laser beam having a pulse width below a few hundred femtoseconds;
an objective lens for directing the pulsed laser beam to a patient's eye; and
an optical system for directing the pulsed laser beam from the laser to the objective lens along an optical path, comprising:
a plurality of chirped mirrors disposed along an optical path of the pulsed laser beam; and
one or more optical elements disposed along the optical path, the optical elements including one or more of: half wave plate, beam splitter, beam sampler, XY beam position scanner and Z beam position scanner,
wherein the plurality of chirped mirrors includes a first chirped mirror, a second chirped mirror, a third chirped mirror, and a fourth chirped mirror disposed sequentially in the optical path in an order of from the first to the fourth chirped mirrors, wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens, and
wherein the one or more optical elements are disposed between the third and fourth chirped mirrors or between the first and second chirped mirrors.

5. The pulsed laser system of claim 4, wherein the first chirped mirror is disposed to receive the pulsed laser beam from the laser.

6. The pulsed laser system of claim 4, wherein the fourth chirped mirror is disposed to reflect the pulsed laser beam to the objective lens.

7. The optical system of claim 1, wherein the first to fourth chirped mirrors provide a combined negative GDD of approximately −18,000 $fs^2$ in the defined wavelength range.

8. The optical system of claim 1, wherein the first and second chirped mirrors provide identical negative GDD to the pulsed laser beam, and the third and fourth chirped mirrors provide identical negative GDD to the pulsed laser beam, and wherein the pulsed laser beam is incident on the first and second chirped mirrors at identical incident angles and is incident on the third and fourth chirped mirrors at identical incident angles.

9. A optical system for directing a pulsed laser beam from a laser to an objective lens, the optical system comprising:
a plurality of chirped mirrors disposed along an optical path of the pulsed laser beam; and
one or more optical elements disposed along the optical path, the optical elements including one or more of: half wave plate, beam splitter, beam sampler, XY beam position scanner and Z beam position scanner,
wherein the plurality of chirped mirrors includes a first chirped mirror, a second chirped mirror, a third chirped mirror, and a fourth chirped mirror disposed sequentially in the optical path in an order of from the first to the fourth chirped mirrors, and wherein the first and second chirped mirrors are non-parallel to each other, or the third and fourth chirped mirrors are non-parallel to each other, wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens.

10. The pulsed laser system of claim 4, wherein the first to fourth chirped mirrors provide a combined negative GDD of approximately −18,000 $fs^2$ in the defined wavelength range.

11. The pulsed laser system of claim 4, wherein the first and second chirped mirrors provide identical negative GDD to the pulsed laser beam, and the third and fourth chirped mirrors provide identical negative GDD to the pulsed laser beam, and wherein the pulsed laser beam is incident on the first and second chirped mirrors at identical incident angles and is incident on the third and fourth chirped mirrors at identical incident angles.

12. The pulsed laser system of claim 4, wherein the laser include no diffraction gratings, prisms or grisms and includes no mechanical actuators.

13. A pulsed laser system for ophthalmic applications, comprising:
a laser generating a pulsed laser beam having a pulse width below a few hundred femtoseconds;
an objective lens for directing the pulsed laser beam to a patient's eye; and
an optical system for directing the pulsed laser beam from the laser to the objective lens along an optical path, comprising:
a plurality of chirped mirrors disposed along an optical path of the pulsed laser beam; and
one or more optical elements disposed along the optical path, the optical elements including one or more of: half wave plate, beam splitter, beam sampler, XY beam position scanner and Z beam position scanner,
wherein the plurality of chirped mirrors includes a first chirped mirror, a second chirped mirror, a third chirped mirror, and a fourth chirped mirror disposed sequentially in the optical path in an order of from the first to the fourth chirped mirrors, and wherein the first and second chirped mirrors are non-parallel to each other, or the third and fourth chirped mirrors are non-parallel to each other, and wherein each of the plurality of chirped mirrors is disposed to reflect the pulsed laser beam only once along the optical path, wherein each of the plurality of chirped mirrors provides a negative group delay dispersion (GDD) per bounce to the pulsed laser beam in a defined wavelength range, and wherein the plurality of chirped mirrors provide a combined negative GDD which is approximately identical in absolute value to a combined positive GDD of the one or more optical elements and the objective lens.

14. The optical system of claim 9, wherein the first chirped mirror is disposed to receive the pulsed laser beam from the laser, and the fourth chirped mirror is disposed to reflect the pulsed laser beam to the objective lens.

15. The optical system of claim 9, wherein the first to fourth chirped mirrors provide a combined negative GDD of approximately −18,000 fs$^2$ in the defined wavelength range.

16. The optical system of claim 9, wherein the first and second chirped mirrors provide identical negative GDD to the pulsed laser beam, and the third and fourth chirped mirrors provide identical negative GDD to the pulsed laser beam, and wherein the pulsed laser beam is incident on the first and second chirped mirrors at identical incident angles and is incident on the third and fourth chirped mirrors at identical incident angles.

17. The pulsed laser system of claim 13, wherein the first chirped mirror is disposed to receive the pulsed laser beam from the laser, and the fourth chirped mirror is disposed to reflect the pulsed laser beam to the objective lens.

18. The pulsed laser system of claim 13, wherein the first to fourth chirped mirrors provide a combined negative GDD of approximately −18,000 fs$^2$ in the defined wavelength range.

19. The pulsed laser system of claim 13, wherein the first and second chirped mirrors provide identical negative GDD to the pulsed laser beam, and the third and fourth chirped mirrors provide identical negative GDD to the pulsed laser beam, and wherein the pulsed laser beam is incident on the first and second chirped mirrors at identical incident angles and is incident on the third and fourth chirped mirrors at identical incident angles.

20. The pulsed laser system of claim 13, wherein the laser include no diffraction gratings, prisms or grisms and includes no mechanical actuators.

\* \* \* \* \*